US008828358B2

(12) United States Patent
Montes et al.

(10) Patent No.: US 8,828,358 B2
(45) Date of Patent: *Sep. 9, 2014

(54) IN SITU FORMATION OF AN ARTIFICIAL BLOCKAGE TO CONTROL BLEEDING BY POLYMER EXPANSION WITH HYDROGEN PEROXIDE

(75) Inventors: Joseph G. Montes, Baltimore, MD (US); Krishnaswamy Kasthuri Rangan, Fairfax, VA (US); Ramachandran Radhakrishnan, Fairfax, VA (US); Tirumalai Srinivas Sudarshan, Vienna, VA (US)

(73) Assignee: Materials Modifications, Inc., Fairfax, VA (US)

( * ) Notice: Subject to any disclaimer, the term of this patent is extended or adjusted under 35 U.S.C. 154(b) by 1008 days.

This patent is subject to a terminal disclaimer.

(21) Appl. No.: 12/073,822

(22) Filed: Mar. 11, 2008

(65) Prior Publication Data

US 2009/0232876 A1    Sep. 17, 2009

(51) Int. Cl.
| | |
|---|---|
| A61K 9/46 | (2006.01) |
| A61K 9/12 | (2006.01) |
| A61K 33/40 | (2006.01) |
| A61P 7/04 | (2006.01) |
| A61K 9/00 | (2006.01) |
| A61K 45/06 | (2006.01) |
| A61K 33/22 | (2006.01) |
| A61K 33/44 | (2006.01) |
| A61K 38/38 | (2006.01) |
| A61K 31/717 | (2006.01) |

(Continued)

(52) U.S. Cl.
CPC ............. *A61K 31/765* (2013.01); *A61K 9/0019* (2013.01); *A61K 9/0007* (2013.01); *A61K 45/06* (2013.01); *A61K 33/22* (2013.01); *A61K 2300/00* (2013.01); *A61K 2201/045* (2013.01); *A61K 33/44* (2013.01); *A61K 38/38* (2013.01); *A61K 31/717* (2013.01); *A61L 2400/04* (2013.01); *A61L 24/04* (2013.01); *A61K 38/1709* (2013.01); *A61K 33/40* (2013.01); *A61K 31/78* (2013.01); *A61K 38/39* (2013.01); *A61K 35/20* (2013.01); *A61K 9/0024* (2013.01); *A61K 31/722* (2013.01)
USPC ............... 424/44; 424/43; 424/616; 424/447; 424/423; 424/487

(58) Field of Classification Search
None
See application file for complete search history.

(56) References Cited

U.S. PATENT DOCUMENTS 2,598,127 A * 5/1952 Keckler .......................... 521/70
4,030,504 A    6/1977 Doyle (Continued)

FOREIGN PATENT DOCUMENTS

WO    WO 2007/088038    *    8/2007    .............. A61L 26/00

OTHER PUBLICATIONS

Palm, M. D. et al. Dermatol. Surg. E-pub Jan. 31, 2008; 431-445.*

(Continued)

*Primary Examiner* — Kevin S Orwig
(74) *Attorney, Agent, or Firm* — Dinesh Agarwal, P.C.

(57) ABSTRACT

A composition for in situ formation of an artificial blockage to control bleeding includes a suitable amount of a polymer-forming component, a suitable amount of a crosslinking agent, hydrogen peroxide, and a decomposing agent for hydrogen peroxide. The decomposing agent includes exogenous or endogenous catalase, or both.

5 Claims, 4 Drawing Sheets

(51) Int. Cl.

| | |
|---|---|
| A61K 31/765 | (2006.01) |
| A61L 24/04 | (2006.01) |
| A61K 38/17 | (2006.01) |
| A61K 31/78 | (2006.01) |
| A61K 38/39 | (2006.01) |
| A61K 35/20 | (2006.01) |
| A61K 31/722 | (2006.01) |

(56) References Cited

U.S. PATENT DOCUMENTS

| | | | |
|---|---|---|---|
| 4,331,653 A | | 5/1982 | Brown et al. |
| 4,377,159 A | | 3/1983 | Hansen |
| 4,948,575 A | * | 8/1990 | Cole et al. ............ 424/44 |
| 4,987,893 A | | 1/1991 | Salamone et al. |
| 5,103,812 A | | 4/1992 | Salamone et al. |
| 5,153,231 A | | 10/1992 | Bouquet et al. |
| 5,336,163 A | | 8/1994 | DeMane et al. |
| 5,507,721 A | | 4/1996 | Shippert |
| 5,667,501 A | | 9/1997 | Fowler et al. |
| 5,846,567 A | | 12/1998 | Kalloo et al. |
| 6,054,122 A | | 4/2000 | MacPhee et al. |
| 6,534,016 B1 | | 3/2003 | Cohen et al. |
| 6,627,216 B2 | | 9/2003 | Brandt et al. |
| RE38,431 E | | 2/2004 | Miekka et al. |
| 6,958,154 B2 | | 10/2005 | Andolino Brandt et al. |
| 6,964,782 B1 | * | 11/2005 | Smith et al. ............ 424/616 |
| 7,101,862 B2 | | 9/2006 | Cochrum et al. |
| 7,196,054 B1 | | 3/2007 | Drohan et al. |
| 7,226,615 B2 | | 6/2007 | Yüksel et al. |
| 7,347,850 B2 | | 3/2008 | Sawhney |
| 7,641,893 B2 | | 1/2010 | Salamone et al. |
| 7,795,326 B2 | | 9/2010 | Salamone et al. |
| 7,838,716 B2 | | 11/2010 | De Luis et al. |
| 8,025,650 B2 | | 9/2011 | Anderson et al. |
| 2003/0224054 A1 | | 12/2003 | Gibbins et al. |
| 2005/0070616 A1 | | 3/2005 | Champ et al. |
| 2006/0142684 A1 | * | 6/2006 | Shanbrom ............ 602/41 |
| 2006/0233887 A1 | | 10/2006 | Day |
| 2007/0203062 A1 | | 8/2007 | Ellis-Behnke et al. |
| 2009/0093550 A1 | * | 4/2009 | Rolfes et al. ............ 514/772.7 |
| 2009/0202617 A1 | | 8/2009 | Ward et al. |
| 2009/0210002 A1 | | 8/2009 | Salamone et al. |
| 2009/0232877 A1 | | 9/2009 | Montes et al. |
| 2010/0063434 A1 | | 3/2010 | Naik |
| 2010/0100022 A1 | | 4/2010 | Greener et al. |
| 2010/0234784 A1 | | 9/2010 | Hartwell |
| 2010/0292626 A1 | | 11/2010 | Gundersen et al. |
| 2011/0046262 A1 | | 2/2011 | Bublewitz et al. |
| 2011/0092871 A1 | | 4/2011 | Fabo et al. |
| 2011/0178451 A1 | | 7/2011 | Robinson et al. |
| 2011/0237994 A1 | | 9/2011 | Russ et al. |
| 2011/0275972 A1 | | 11/2011 | Rosenberg |

OTHER PUBLICATIONS

Costa, S. A. et al. Ch. 17 in Biodegradable Systems in Tissue Engineering and Regenerative Medicine; Rui Reis, ed. CRC Press; 2004.*

PCT International Search Report and the Written Opinion in International App. No. PCT/US09/06536 ( 8 pp.), Feb. 26, 2010.

B.S. Kheirabadi, D. Tuthill, R. Pearson, V. Bayer, D. Beall, W. Drohan, M. J. MacPhee, J.B. Holcomb, Metabolic and Hemodynamic Effects of $CO_2$ Pneumoperitoneum in a Controlled Environment, *Journal of Trauma Injury, Infection and Ciritcal Care*, 50, 1031-1043 (2001).

J.B. Holcomb, J.M. McClain, A.E. Pusateri, D. Beall, J.M. Macaitis, R.A. Harris, M. J. MacPhee, J.R. Hess, Fibrin Sealant Foam Sprayed Directly on Liver Injuries Decreases Blood Loss in Resuscitated Rats *Journal of Trauma Injury, Infection and Ciritcal Care*, 49, 246-250, (2000).

D.D. Tuthill, V. Bayer, A.M. Gallagher,W.N. Drohan, M.J. MacPhee, Assessment of Topical Hemostats in a Renal Hemorrhage Model in Heparinized Rats, *Journal of Surgical Research*, 95, 126-132 (2001).

Holcomb et al. Implications of a New Dry Fibrin Sealant Technology for Trauma Surgery, *Surgical Clinics of North America*, 77, 944-952 (1997).

H.B. Alam, G. B. Uy, D. Miller, E. Koustova T. Hancock, R. Inocencio, D. Anderson, O. Llorente, P. Rhee, Comparative Analysis of Hemostatic Agents in a Swine Model of Lethal Groin Injury, *The Journal of Trauma, Injury, Infection, and Critical Care*, 54, 1077-1082 (2003).

R.G. Ellis-Behnke, Y-X. Liang, D.K.C. Tay, P.W.F. Kau, G.E. Schneider, S. Zhang, W. Wu, K.-F. So, Nano Hemostat Solution: Immediate Hemostasis at the Nanoscale, *Nanomedicine: Nanotechnology, Biology, and Medicine*; 2 , 207-215 (2006).

M.W. Chan, S.D. Schwaitzberg, M. Demcheva, J. Vournakis, S. Finkielsztein, R.J. Connolly, Comparison of Poly-N-acetyl Glucosamine with Absorbable Collagen, and Fibrin Sealant for Achieving Hemostasis in a Swine Model of Splenic Hemorrhage, *Journal of Trauma Injury, Infection and Critical Care*, 48, 454-7 (2000).

I. Wedmore, J.G. McManus, A.E. Pusateri, J.B. Holcomb, Special Report on the Chitosan-based Hemostatic Dressing: Experience in Current Combat Operations, *The Journal of Trauma Injury, Infection and Critical Care*, 60, 655-658 (2006).

A. M. Pope, Editor, Fluid Resuscitation: State of the Science for Treating Combat Casualties and Civilian Injuries, The National Academy Press, (2000).

A.E. Pusateri,J.B. Holcomb, B.S. Kheirabadi,H.B. Alam, C.E. Wade, K.L. Ryan, Making Sense of the Preclinical Literature on Advanced Hemostatic Products, *The Journal of Trauma Injury, Infection and Critical Care*, 60, 674-682, (2006).

H.B. Alam, Z. Chen, A. Jaskille,R.I.L.C. Querol, E. Koustova, R. Inocencio, R. Conran, A. Seufert, N. Ariaban, K. Toruno, P. Rhee, Application of a Zeolite Hemostatic Agent Acheives 100% Survival in a Lethal Model of Complex Groin Injury in Swine, *The Journal of Trauma Injury, Infection and Critiacal Care*, 56, 974-983, (2004).

B.S. Kheirabadi, E.M. Acheson, R. Deguzman, J.L. Sondeen, K.L. Ryan, A. Delgado A, E.J. Dick Jr, J.B. Holcomb, Hemostatic Efficacy of Two Advanced Dressings in an Aortic Hemorrhage Model in Swine, *The Journal of Trauma Injury, Infection and Critical Care*, 59, 25-34 (2005).

J.G McManus, I. Wedmore, Modern Hemostatic Agents for Hemorrhage Control—A review and Discussion of Use in Current Combat Operations, *Business Briefing: Emergency Medicine Review*,76-79 (2005).

Office Action dated Feb. 4, 2011, in U.S. Appl. No. 12/314,718, filed Dec. 16, 2008.

Office Action (Restriction Requirement) dated Sep. 29, 2010, in U.S. Appl. No. 12/314,718, filed Dec. 16, 2008.

Li X, Xu A, Xie H, Yu W, Xie W, Ma X. Preparation of low molecular weight alginate by hydrogen peroxide depolymerization for tissue engineering. Carbohydrate Polymers 79 (2010) 660-664.

PCT International Search Report and the Written Opinion in International App. No. PCT/US2012/050716 dated Oct. 19, 2012 (13 pp.) with Search History (11 pp.).

Office Action dated Aug. 10, 2011, in U.S. Appl. No. 12/314,718, filed Dec. 16, 2008.

Office Action dated Oct. 24, 2013, in U.S. Appl. No. 12/314,718, filed Dec. 16, 2008.

Office Action dated Feb. 25, 2014, in U.S. Appl. No. 13/584,852, filed Aug. 14, 2012.

Office Action (Restriction Requirement) dated Oct. 29, 2013, in U.S. Appl. No. 13/584,852, filed Aug. 14, 2012.

Haller, G. et al. Oxygen embolism after hydrogen peroxide irrigation of a vulvar abscess, *British Journal of Anaesthesia* 88 (4): 597-9 (2002).

Shetty, K. Hydrogen Peroxide Burn of the Oral Mucosa, The *Annals of Pharmacotherapy*, vol. 40, p. 351, Feb. 2006.

Rackoff, W.R. et al. Gas Embolism After Ingestion of Hydrogen Peroxide, *Pediatrics*, vol. 85, No. 4, Apr. 1990, 593-594

Li, Y. Biological Properties of Peroxide-containing Tooth Whiteners, *Food and Chemical Toxicology* 34 (1996) 887-904.

Giberson, T.P. et al. Near-Fatal Hydrogen Peroxide Ingestion, *Annals of Emergency Medicine*, 18:7, Jul. 1989, 778-779.

* cited by examiner

IN SITU FORMATION OF AN ARTIFICIAL BLOCKAGE TO CONTROL BLEEDING BY POLYMER EXPANSION WITH HYDROGEN PEROXIDE

FIELD AND BACKGROUND OF THE INVENTION

The present invention is generally directed to hemostatic compositions and methods employing the same, the delivery of agents into or unto wounds and/or body cavities, and more particularly to a composition and method for controlling bleeding at wound sites through the formation of an in situ obstruction to blood flow.

One of the major causes of death is uncontrolled loss of blood due to traumatic injury, accidental or otherwise. The blood loss may be internal or external and, when not restricted or controlled quickly, can be fatal. It is, therefore, critical to restrict, arrest, or control blood loss by managing a wound by, for example, creating a physical obstruction. Various prior art methods and compositions disclose the medical use of hydrogen peroxide as an antiseptic for wounds and/or hemostasis-promoting agent, e.g., U.S. Pat. No. 5,846,567, as a vapor for the dispersal or creation of a gel, and U.S. Pat. No. 5,667,501, for stimulation action of hydrogen peroxide in fibroblast proliferation and its application in wound dressing. However, none rely on the interaction between catalase and hydrogen peroxide to drive a foam or other substance into a wound space or other body cavity.

OBJECTS AND SUMMARY OF THE INVENTION

The principal object of the present invention is to provide a composition and method for reducing, restricting, and/or arresting, (collectively "controlling") hemorrhage from wounds, internal or external, in humans and other animals.

Another object of the present invention is to provide a composition and method for in situ formation of an artificial blockage to control bleeding.

Another object of the present invention is to provide a composition and method for controlling bleeding due to any traumatic injury, deliberate, as in a medical procedure, or accidental, particularly when bleeding occurs from puncture or other penetration wounds. The invention works by, one or more of, 1) increasing the efficiency of delivery or dispersal of hemostatic and/or other wound-treatment agent(s) and/or any other agent via the selective expansion of substance(s) containing the agent(s), as the expansion is most rapid where blood and other body fluids containing catalase are most concentrated; 2) providing a pressurized wound or other compartment that will restrict blood flow and loss within the compartment; 3) providing antiseptic in the form of unreacted hydrogen peroxide to the surface(s) and space(s) of the wound(s) and/or any other body space; 4) providing means for the creation of an artificial clot, tamponade, or obstruction that can fill the wound space(s) and/or other body space(s) efficiently; 5) providing excess oxygen where it may aid in initial healing; 6) in certain cases, providing the chemical basis for accelerating and/or making possible other chemical reactions, produced from extraneously applied chemicals and/or from endogenous (originating from the body itself) chemicals, leading to formation of a foam, and/or obstruction to bleeding or both and 7) in the case of treatment of wounds, promotion of clotting by the hydrogen peroxide itself.

Another object of the present invention is to provide a composition and method for controlling bleeding that is unique in relying on the interaction between hydrogen peroxide and catalase, the latter being distributed inside or upon the wound according to the distribution of leaked blood and other body fluids, so that expansion of an applied substance or agent to the wound or other body space will result in a self-regulating process whereupon the oxygen-releasing reaction will favor those locations where it is needed the most.

Another object of the present invention is to provide a composition and method for controlling bleeding wherein one or more agents containing hydrogen peroxide are administered to a wound and/or other body space or surface, causing expansion and/or foaming of a substance thereupon due to oxygen release catalyzed by localized catalase. The expanded substance may be a viscous liquid, semi-solid, or solid substance that acts as an artificial blood clot or clog under pressure, stemming the flow of blood from the wound, as in the case of viscous drag. Examples of such expanded substances include: a polyurethane, polylactic acid, polyacrylic acid, polyvinylchloride, a polysaccharide, and polyvinyl alcohol.

Another object of the present invention is to provide a kit for in situ formation of an artificial blockage in a wound or body cavity.

In summary, the present invention provides a method and composition for controlling bleeding, internal or external, by in situ formation of a blockage.

One of the above objects is met, in part, by the present invention, which in one aspect includes a composition for in situ formation of an artificial blockage to control bleeding. The composition includes a suitable amount of a polymer-forming component, a suitable amount of a crosslinking agent, hydrogen peroxide, and a decomposing agent for hydrogen peroxide. The decomposing agent includes exogenous and/or endogenous catalase. The composition may also include one or more anesthetics, one or more procoagulant(s) or coagulants, and one or more vasoconstrictors. Anesthetics may be at least one member taken from the group of tetracaine, lidocaine, benzocaine, procaine, and a combination thereof; procoagulants or coagulants may be at least one member selected from the group consisting of tissue factor, Factor VII, Factor VIIa, prothrombin, thrombin, Factor XII, Factor XIII, Factor XIIIa, fibrinogen, fibrin monomer, fibrin multimer, crosslinked fibrin, and a combination thereof; vasoconstrictors may be at least one member selected from the group consisting of oxymetazoline, oxymetazoline derivative, phenylephrine, phenylpropanolamine, nicotine, pseudoephedrine, ephedrine, ephedrine derivative, and a combination thereof.

Another aspect of the present invention includes a composition for in situ formation of an artificial blockage to control bleeding, which includes a component that can expand, a gas-generating agent, and endogenous or exogenous catalase, or both.

Another aspect of the present invention includes a method for in situ formation of an artificial blockage in a wound or body cavity, which includes providing a suitable amount of a polymer-forming component, providing a suitable amount of a crosslinking agent, providing hydrogen peroxide as part of the polymer-forming component or the crosslinking agent, delivering the polymer-forming component and the crosslinking agent separately, but substantially simultaneously in a wound or body cavity, thereby allowing mixing thereof, and allowing the mixture to come in contact with endogenous catalase thereby producing an expanded mass. The polymer-forming component or components may be at least one member taken from the group consisting of polymers, including polyacrylate, polyvinyl alcohol, polyvinyl pyrrolidone, polyethylene glycol, polyethylene amine, polyacrylamide, polylysine, chitosan, polysaccharide, whey protein, casein, albumin, collagen, catalase, gelatin, a polypeptide or protein possessing reactive groups capable of crosslinking to isocyanates, diisocyanates, or other molecules; starch, cellulose, polylactic acid, a polyol, and a combination thereof. The crosslinking agent may be at least one member selected from the group consisting of phosphoric acid, boric acid, glutaraldehyde, acetaldehyde, a diisocyanate, a carbodiimide, calcium ion, genipin, and a combination thereof. The polymer formed comprises at least one member taken from the group of polyvinyl chloride, polyvinyl acetate, polyacrylic acid, polylactic acid, polylysine, polyserine, polythreonine, a polypeptide or protein, polyacrylamide, a polyurethane, a polysaccharide, and a combination thereof.

Another aspect of the present invention includes a method for in situ formation of an artificial blockage in a wound or body cavity, which includes providing a first component containing a gas-generating agent, providing a second component including an expandable component, and the enzyme catalase, delivering the first and second components separately, but substantially simultaneously in a wound or body cavity, allowing catalase to come in contact with the gas-generating agent thereby producing a gas, and allowing the gas to come in contact with the expandable component thereby producing an expanded mass.

Another aspect of the present invention includes a kit for in situ formation of an artificial blockage in a wound or body cavity, which includes a first component including hydrogen peroxide, a second component including an expandable component, catalase and instructions for using the components and an optional bandage.

BRIEF DESCRIPTION OF THE DRAWINGS

One of the above and other objects, novel features and advantages of the present invention will become apparent from the following detailed description of the preferred embodiment(s) of invention, illustrated in the accompanying drawings, wherein.

DETAILED DESCRIPTION OF THE PREFERRED EMBODIMENT(S) OF THE INVENTION

Figure 1:
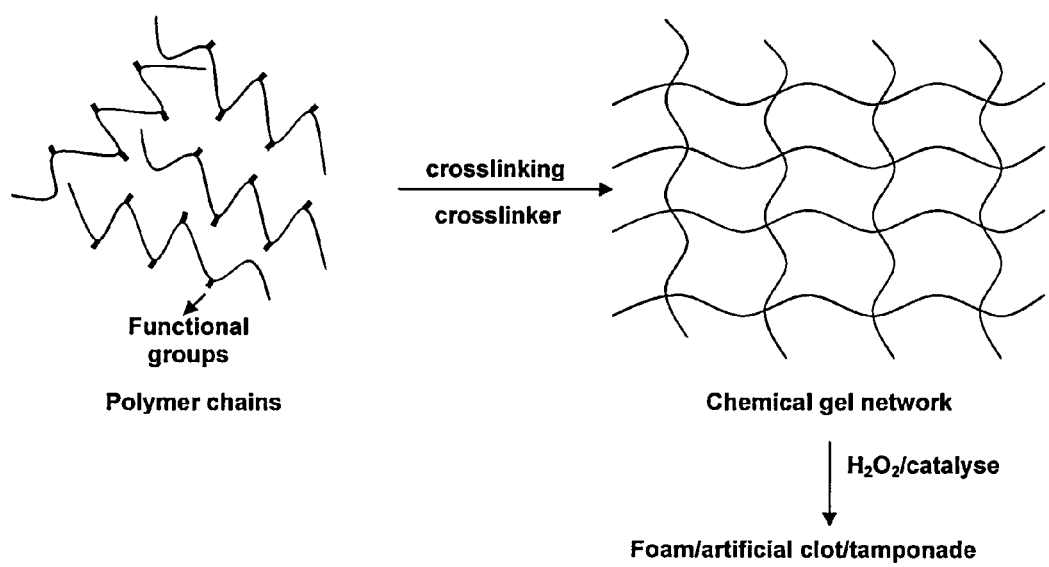
FIG. 1 is a schematic illustration of an exemplary reaction between various components of the present invention.

The method described herein is conveniently referred to as catalase/hydrogen peroxide reaction-driven expansion, dispersal, and spatial configuring of wound with hemostatic and/or other wound treatment agent(s) and/or other agents that can be delivered into any body cavity or space, including wounds. The method can be applied to both humans and non-human animals.

The method allows filling of wound or other space, open to air or otherwise, to allow coating of a body surface with a substance in the form of foam or other material by pressure produced through the release of oxygen consequent to the reaction of the enzyme catalase with hydrogen peroxide. With this method, an agent(s) or substance(s), containing hydrogen peroxide, when injected through the opening of a wound or other space or cavity in the body, will expand, disperse, and/or configure to fill the wound or other space when the agent encounters blood or other body fluid bearing endogenous catalase, and thus will assist hemostasis by effecting the improved delivery of hemostatic agent, while at the same time causing a pressurized obstruction to bleeding or other physiological flow.

Alternatively, a binary system of two components, preferably one containing catalase and the other hydrogen peroxide, when injected or forced into a wound space or other body cavity, simultaneously will react to drive the two components of the system, and/or their reaction products, into or unto the wound or other body space or surface, distributing the agents to where most needed, while at the same time creating a physical obstruction that restricts blood loss.

The method for delivery of the hydrogen peroxide and other substances into the wound 10 (FIG. 2A) or other body space will preferably be effected through manual compression of a pliable tube or piston-dependent delivery device 12 (FIG. 2A) containing the deliverable agents, so that hydrogen peroxide and other agents (FIG. 2A—components A and B) will pass into the wound space or other body space, although other suitable means may also be employed. Typically, two or more small tubing extensions 14 and 16 from the delivery device 12 will be fed into the wound 10 or other body space to accomplish the method. Once the agent, containing the hydrogen peroxide, makes contact with catalase, typically present in blood and other body fluids, foaming or expansion of the applied or formed agent will result, filling the space in the wound or other body space (FIG. 2B). The foam or other expanded substance may, over time, harden or become more viscous, including transforming from one phase to another, such as from liquid to semi-solid or solid, and may include polymer-forming ingredients and/or polymer formed from such ingredients, creating an artificial clot or clog, driven into place and shaped by the oxygen release resulting from the interaction between hydrogen peroxide and catalase.

Preferably, two components will be mixed simultaneously just prior to or just after injection, insertion, or any other kind of application to a wound space. At least one of these two binary components will contain hydrogen peroxide at a concentration between about 0.000001% to about 100% by volume or weight, with a preferred range being between about 3% to about 20%, and a more preferred concentration being about 5%.

The composition of the present invention preferably includes an expandable component, such as a polymer precursor; a gas-generating component, such as hydrogen peroxide; and a decomposing agent for the gas-generating agent. The decomposing agent includes endogenous and/or exogenous catalase.

The concentration of catalase can vary from 0 to about five thousand milligrams per milliliter (mL), with a preferred range of about 50 to about 300 milligrams per mL, and a more preferred concentration of about 150 milligrams per milliliter (mL).

The medium bearing the components delivered by the method of the invention can be of any state of matter, including but not limited to liquid, gas, or solid, or any combination thereof.

Other agents in the composition may include polymers, organic and/or inorganic, polymer-forming ingredients, linking or crosslinking agents, gas-generating agents other than hydrogen peroxide or catalase, procoagulants, coagulants, anesthetics, vasoconstrictors, enzymes (including catalase), pastes, liquids, organic or inorganic. An example of a chemical reaction between catalase and two matrix components (one of the two containing hydrogen peroxide) of the composition used in the method, is shown below.

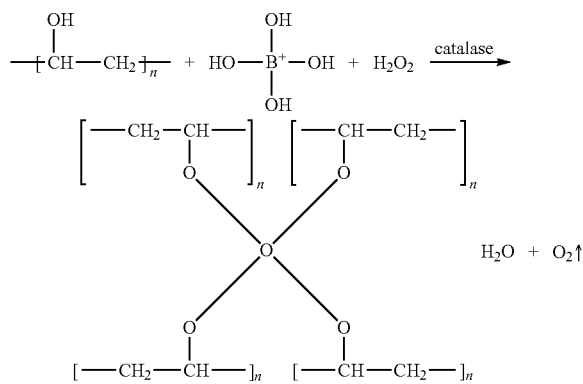

Non-limiting examples of polymer-forming polymers, include: polyacrylate, polyvinyl alcohol, polyvinyl pyrrolidone, polyethylene glycol, polyethylene amine, polyacrylamide, polylysine, chitosan, polysaccharides, whey protein, casein, albumin, collagen, catalase, gelatin, a polypeptide or protein possessing reactive groups capable of crosslinking to isocyanates, diisocyanates, or other molecules; starch, cellulose, polylactic acid, a polyol, and a combination thereof.

Non-limiting examples of crosslinking agents, include: phosphoric acid, boric acid, glutaraldehyde, acetaldehyde, calcium ions, and genepin.

Non-limiting examples of coagulants and procoagulants, include: tissue factor, Factor VII, Factor VIIa, prothrombin, thrombin, Factor XII, Factor XII, Factor XIIIa, fibrinogen, fibrin monomer, fibrin multimer, and crosslinked fibrin.

Non-limiting examples of vasoconstrictors, include: oxymetazoline, oxymetazoline derivatives, phenylephrine, phenylpropanolamine, nicotine, pseudoephedrine, ephedrine, and ephedrine derivatives.

The system used to deliver any of the above-mentioned agents, including the agent hydrogen peroxide, to a wound or body cavity can be any kind or property. The volume of the component(s) to be delivered, or the total volume of component(s) actually delivered, can range from about 0.0000001 to about 10,000,000 milliliters (mL), with a preferred range of about 5 mL to about 50 mL, and a more preferred volume of about 10 mL.

After allowing some time, preferably about 5 seconds to two minutes, or more preferably about 45 seconds, for expansion or pressurization of the component(s) or resulting component(s) in the wound space or body cavity, the wound will be sealed with a suitable bandage. The amount of time before application of the bandage can be from 0 to about 1,000,000 seconds (sec) after delivery of the component(s), with a preferred range of about 1 sec to about 15 minutes (min), and a more preferred interval of about 2 min.

Figure 2A:
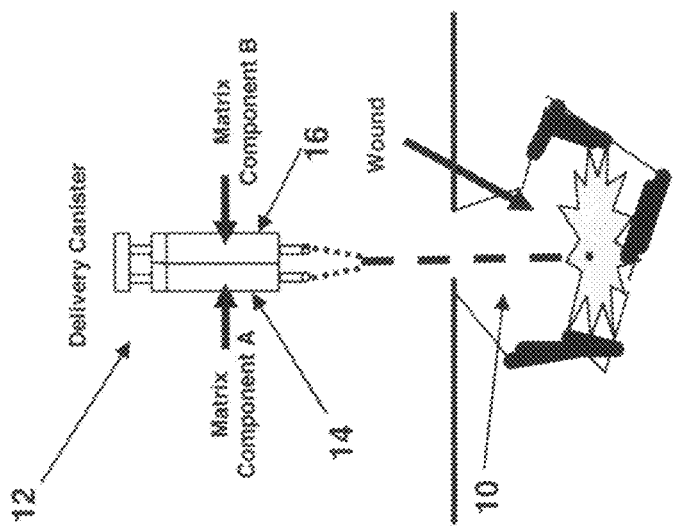
FIGS. 2A and 2B are schematic illustrations showing the mechanism of formative action due to an interaction between hydrogen peroxide and blood.
Figure 2B:
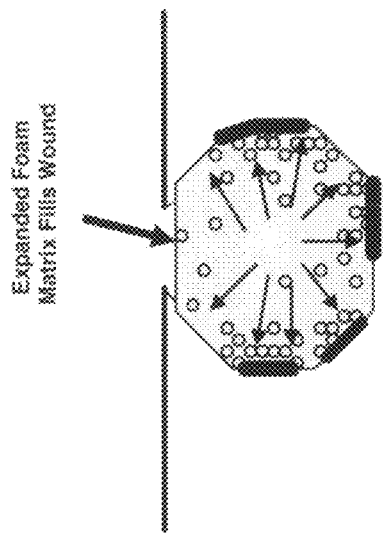

The mechanism of formation of the clotting material that fills the wound and enhances delivery of matrix components is illustrated in FIG. 2A-2B.

Example 1

Figure 3:
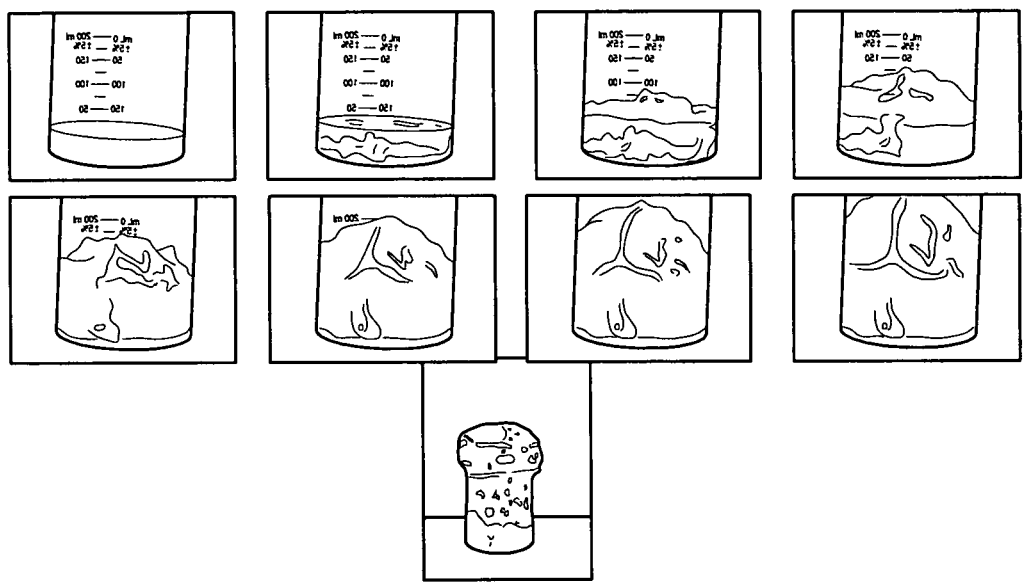
FIG. 3 shows time-lapse images in time sequence, each frame about two seconds apart, except for the last frame, taken 15 seconds after mixing of the binary components in the presence of manganese dioxide (substituting for catalase in blood) at bottom of beaker.

Solution A was prepared by mixing 1% solution of hydrogen peroxide with 5% solution of polyvinyl alcohol (Average M.W. 140000). Solution B was prepared by dissolving boric acid in water to form a 5% solution. Equal volume of solutions A and B were mixed in the presence of manganese dioxide in a glass beaker. Instantaneously, foam formed in copious amount and expanded to cover the entire volume of the beaker. A frame-by-frame photographic sequence of expansion of the composition is illustrated in FIG. 3.

Example 2

Figure 4:
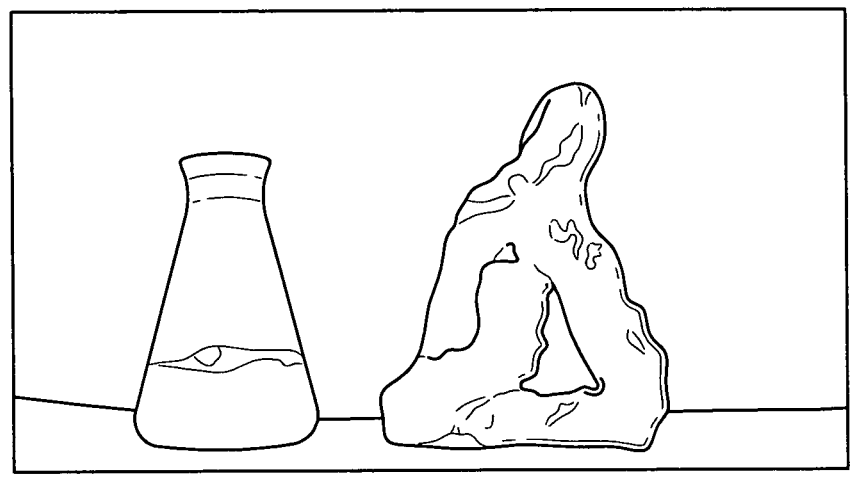
FIG. 4 is a photograph showing the formative action of the composition of the invention on contact with blood (naturally containing catalase).

The reaction in Example 1 was repeated with one exception. Human blood was substituted for manganese dioxide. Foam resulted immediately, expanding to cover the entire volume of the container. Photograph of the reaction product is shown in FIG. 4.

The composition of the present invention can be of any chemical or physical nature or properties, and may include any organic or inorganic substance or combination of substances.

The composition of the present invention may include a catalyst such as triethylenediamine (TEDA, also known as 1,4-diazabicyclo[2.2.2]octane or DABCO), dimethylcyclohexylamine (DMCHA), dimethylethanolamine (DMEA), tetramethylbutanediamine (TMBDA), pentamethyldipropylenetriamine, N-(3-dimethylaminopropyl)-N,N-diisopropanolamine, 1,3,5-(tris(3-dimethylamino)propyl)-hexahydro-s-triazine, bis-(2-dimethylaminoethyl)ether, N-ethylmorpholine, triethylamine(TEA), 1,8-diazabicyclo[5.4.0]undecene-7 (DBU), pentamethyldiethylenetriamine (PMDETA), benzyldimethylamine (BDMA), and tetracaine or any other tertiary amine.

While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

REFERENCES

The following references, and any cited in the disclosure herein, are hereby incorporated herein in their entirety by reference.

1. A. Brandt, C. M. Leir, D. J. Wirtanen, Spray Bandage and Drug Delivery System, U.S. Pat. No. 6,958,154 (2005).
2. M. J. MacPhee, W. N. Drohan, C. J. Woolverton, Supplemented and Unsupplemented Tissue Sealants, Methods of their Production and Use, U.S. Pat. No. 6,054,122 (2000).
3. W. N. Drohan, M. J. MacPhee, H. Nunez, G. Liau, T. Maciag, W. H. Burgess, Methods for Treating Wound Tissue and Forming a Supplemented Fibrin Matrix U.S. Pat. No. 7,196,054 (2007).
4. S. I. Miekka, W. N. Drohan, T. R. Jameson, J. R. Taylor, Jr, M. P. Singh, M. J. MacPhee, Methods of Production and use of Liquid Formulations of Plasma Proteins U.S. Pat. No. RE38431 (2004).
5. K. C. Cochrum, S. Jemtrud, Hemostatic Compositions and Methods for Controlling Bleeding U.S. Pat. No. 7,101,862 (2006).
6. A. N. Kaloo, P. J. Paricha, Clot Dissolving Method, U.S. Pat. No. 5,846,567 (1998).

7. M. Fowler, T. R. Burrow, T. D. Turner, R. J. Schmidt, L. Y. Chung, Wound Dressings, U.S. Pat. No. 5,667,501 (1997).
8. B. S. Kheirabadi, D. Tuthill, R. Pearson, V. Bayer, D. Beall, W. Drohan, M. J. MacPhee, J. B. Holcomb, Metabolic and Hemodynamic Effects of $CO_2$ Pneumoperitoneum in a Controlled Environment, *Journal of Trauma Injury, Infection and Critical Care,* 50, 1031-1043 (2001).
9. J. B. Holcomb, J. M. McClain, A. E. Pusateri, D. Beall, J. M. Macaitis, R. A. Harris, M. J. MacPhee, J. R. Hess, Fibrin Sealant Foam Sprayed Directly on Liver Injuries Decreases Blood Loss in Resuscitated Rats *Journal of Trauma Injury, Infection and Critical Care,* 49, 246-250, (2000).
10. D. D. Tuthill, V. Bayer, A. M. Gallagher, W. N. Drohan, M. J. MacPhee, Assessment of Topical Hemostats in a Renal Hemorrhage Model in Heparinized Rats, *Journal of Surgical Research,* 95, 126-132 (2001).
11. Holcomb et al. Implications of a New Dry Fibrin Sealant Technology for Trauma Surgery, *Surgical Clinics of North America,* 77, 944-952 (1997).
12. H. B. Alam, G. B. Uy, D. Miller, E. Koustova T. Hancock, R. Inocencio, D. Anderson, O. Llorente, P. Rhee, Comparative Analysis of Hemostatic Agents in a Swine Model of Lethal Groin Injury, *The Journal of TRAUMA, Injury, Infection, and Critical Care,* 54, 1077-1082 (2003).
13. R. G. Ellis-Behnke, Y-X. Liang, D. K. C. Tay, P. W. F. Kau, G. E. Schneider, S. Zhang, W. Wu, K.-F. So, Nano Hemostat Solution: Immediate Hemostasis at the Nanoscale, *Nanomedicine: Nanotechnology, Biology, and Medicine;* 2, 207-215 (2006).
14. M. W. Chan, S. D. Schwaitzberg, M. Demcheva, J. Vournakis, S. Finkielsztein, R. J. Connolly, Comparison of Poly-N-acetyl Glucosamine with Absorbable Collagen, and Fibrin Sealant for Achieving Hemostasis in a Swine Model of Splenic Hemorrhage, *Journal of Trauma Injury, Infection and Critical Care,* 48, 454-7 (2000).
15. I. Wedmore, J. G. McManus, A. E. Pusateri, J. B. Holcomb, Special Report on the Chitosan-based Hemostatic Dressing: Experience in Current Combat Operations, *The Journal of Trauma Injury, Infection and Critical Care,* 60, 655-658 (2006).
16. A. M. Pope, Editor, Fluid Resuscitation: State of the Science for Treating Combat Casualties and Civilian Injuries, The National Academy Press, (2000).
17. A. E. Pusateri, J. B. Holcomb, B. S. Kheirabadi, H. B. Alam, C. E. Wade, K. L. Ryan, Making Sense of the Preclinical Literature on Advanced Hemostatic Products, *The Journal of Trauma Injury, Infection and Critical Care,* 60, 674-682, (2006).
18. H. B. Alam, Z. Chen, A. Jaskille, R. I. L. C. Querol, E. Koustova, R. Inocencio, R. Conran, A. Seufert, N. Ariaban, K. Toruno, P. Rhee, Application of a Zeolite Hemostatic Agent Achieves 100% Survival in a Lethal Model of Complex Groin Injury in Swine, *The Journal of Trauma Injury, Infection and Critical Care,* 56, 974-983, (2004).
19. B. S. Kheirabadi, E. M. Acheson, R. Deguzman, J. L. Sondeen, K. L. Ryan, A. Delgado A, E. J. Dick Jr, J. B. Holcomb, Hemostatic Efficacy of Two Advanced Dressings in an Aortic Hemorrhage Model in Swine, *The Journal of Trauma Injury, Infection and Critical Care,* 59, 25-34 (2005).
20. J. G McManus, I. Wedmore, Modern Hemostatic Agents for Hemorrhage Control—A review and Discussion of Use in Current Combat Operations, *Business Briefing: Emergency Medicine Review,* 76-79 (2005).

What is claimed is:

1. An injection method for in situ formation of a pressurized obstruction in a wound or body cavity to control bleeding, comprising the steps of:
   a) providing a first component comprising hydrogen peroxide having a concentration of about 20% to about 100% by volume or weight;
   b) providing a second component comprising an expandable component comprising polyacrylate;
   c) delivering the first and second components separately, but substantially simultaneously by injection into a wound or body cavity;
   d) allowing blood to come in contact with the hydrogen peroxide, thereby producing a gas; and
   e) allowing the gas to come in contact with the polyacrylate, thereby producing an expanded mass within 5 seconds to 45 seconds forming a pressurized obstruction to control bleeding in the wound or body cavity.

2. The method of claim 1, wherein:
the first and second components are provided in a volume of about 0.1 mL to about 1000 mL.

3. The method claim 1, wherein:
the method may be applied consecutively more than once to the wound or body cavity, within a space of time varying between 0.1 seconds and one year.

4. The method of claim 1, wherein:
the expanded mass substantially entirely fills up the wound or body cavity.

5. The method of claim 1, wherein:
the expanded mass configures to assume the shape of the wound or body cavity.

* * * * *